United States Patent [19]

Shiba et al.

[11] 4,382,080
[45] May 3, 1983

[54] METHOD FOR TREATING AND PREVENTING BACTERIAL INFECTIONS

[75] Inventors: Tetsuo Shiba, Toyonaka; Yuichi Yamamura, Takarazuka; Shozo Kotani, Minoo; Osamu Nagase; Hidemasa Ogawa, both of Minamifunabori, all of Japan

[73] Assignee: Daiichi Seiyaku Co., Ltd., Tokyo, Japan

[21] Appl. No.: 262,244

[22] Filed: May 11, 1981

Related U.S. Application Data

[63] Continuation of Ser. No. 77,808, Sep. 21, 1979, abandoned.

[30] Foreign Application Priority Data

Sep. 21, 1978 [JP] Japan .................... 53-116155

[51] Int. Cl.³ ............................................. A61K 37/00
[52] U.S. Cl. ......................................................... 424/177
[58] Field of Search ........................................... 424/177

[56] References Cited

U.S. PATENT DOCUMENTS 4,082,736  4/1978  Jones et al. ............... 260/112.5 R
4,101,536  7/1978  Yamamura et al. ........ 260/112.5 R
4,153,684  5/1979  Audibert et al. ........... 260/112.5 R
4,272,524  6/1981  Chedid et al. .............. 260/112.5 R Primary Examiner—Delbert R. Phillips
Attorney, Agent, or Firm—Sughrue, Mion, Zinn, Macpeak & Seas

[57] ABSTRACT

A method for treating and preventing bacterial infections which comprises administering a 6-O-acylmuramyl depeptide of the formula:

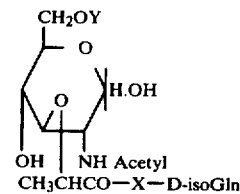

wherein X represents a divalent residual group of an amino acid such as L-alanine, L-serine, L-valine, etc., Y represents a residual group of a middle to higher fatty acid having 10 to 60 carbon atoms and isoGln represents a residual group of isoglutamine, or a pharmaceutical composition containing a 6-O-acylmuramyl dipeptide of the formula(I) as an active ingredient to a patient afflicted therewith.

5 Claims, No Drawings

METHOD FOR TREATING AND PREVENTING BACTERIAL INFECTIONS

This is a continuation of application Ser. No. 77,808, filed Sept. 21, 1979, now abandoned.

BACKGROUND OF THE INVENTION

1. Field of the Invention

This invention relates to a method for treating and preventing bacterial infections which comprises administering a 6-O-acylmuramyl dipeptide of the formula:

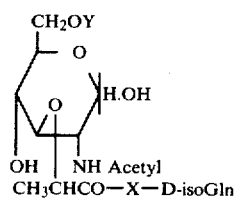

OH | NH Acetyl
CH₃CHCO—X—D-isoGln wherein X represents a residual group of an amino acid such as L-alanine, L-serine, L-valine, etc., Y represents a residual group of a middle to higher fatty acid having 10 to 60 carbon atoms, preferably 15 to 50 carbon atoms and isoGln represents a residual group of isoglutamine.

2. Description of the Prior Art

Recently, remedial and prognostic observations of patients who have fallen into leukaemia, malignant lymphoma, various cancerous diseases and even metabolic insufficiency of the organs have revealed the trend of enhanced frequency of complications of bacterial infections, especially intractable infections (and particularly cases of their terminal infections).

Despite the development of bacteriological exploration, adequate attention paid to treatment, improvement of protective techniques against infection and further propagation of various chemotherapeutic agents, there are general infections and intractable infections leading to death, the background of which may be attributable not only to the reduction in body's resistance to infection of the disease itself, but also to the introgenic factors such as those caused by anti-cancer drugs, immunosuppressive drugs, adrenocortical hormones, etc., especially the hindrance of resistance factors against infections, particularly those possessed by various phagocytes including polymorphonuclear leukocyte. Therefore, there has recently been increasing demand for the development of drugs which possess both preventive and therapeutic effects against the above-mentioned infections. Especially, it is strongly desired to develop a new type of drug which has no direct bacterial effect but prophylactic and therapeutic effects against infections, because at present there are problems aroused in the treatment of the infections due to mild toxic bacteria by the advent of resistant bacteria produced by the abuse of chemotherapeutic agents and the alternation phenomenon of bacteria.

There have heretofore been known a few examples of those having such effects, that is, some strains of Corynebacterium and Mycobacterium, and their cell wall components, liposaccharide (LPS) extracts of gram negative bacteria, etc. However, these failed to serve for the administration to human body because of their side effects such as immunogenisity (antigenicity), pyretogenisity, etc.

More recently, it was reported that N-acetylmuramyl dipeptides possess defense effect against certain becterial infections (Proc. Natl. Acad. Sci. U.S.A. Vol. 74, No. 5, pp. 2089-2093). The effects exhibited by the above-mentioned compounds are, however, not quite satisfactory.

SUMMARY OF THE INVENTION

Accordingly, after intensive study in pursuit of compounds which can be administered to human body and possess excellent preventive and therapeutic effects against infections, we have found that the compounds of the formula (I) above have excellent preventive and therapeutic effects against bacterial infections and thus accomplished the present invention.

DETAILED DESCRIPTION OF THE INVENTION

The present invention is therefore to provide a method for preventing and treating bacterial infections comprising administering a 6-O-acylmuramyl dipeptide of the formula (I) or a pharmaceutical composition containing the 6-O-acylmuramyl dipeptide as an active ingredient to a patient afflicted therewith.

Some of the compounds of the formula (I) above have been disclosed in the applicants' copending Japanese patent application (OPI) No. 46020/1977 (The term "OPI" as used herein refers to a "published unexamined Japanese patent application") and Bull. Chem. Soc. Japan, 51 (7), 2122 (1978) and known as such having an immunity adjuvant activity. Those which are not included in the above-mentioned patent application, etc., can easily be produced in accordance with the procedures disclosed in the above Japanese patent application or Japanese patent application No. 37960/1978.

The excellent preventive and therapeutic effects against infections of the compounds of the formula (I) according to the present invention will be demonstrated in the following examples.

EXAMPLE 1

Inhibitory Effect against Infection

The inhibitory effects against infections of the compounds according to the present invention and the control compounds were determined as follows. Each of the compounds of the present invention was dissolved in phosphate buffer saline (PBS) (pH 7.0) to give a 500 μg/ml solution as calculated as the corresponding control compound. Similarly, Control Compound 1, Control Compound 2 and Control Compound 3 were dissolved in PBS (pH 7.0) to give 500 μg/ml solutions respectively. 0.2 ml of each preparation was intraperitoneally administered 24 hours prior to infection. As shown in Table 1, STD-ddY mice (5 weeks old, 25 g) were infected with *Escherichia coli* E77156, *Pseudomonas aeruginosa* No. 15 and *Klebsiella pneumoniae* SK at two different inoculation levels by injecting subcutaneously on the back. Incidentally, for each bacterium, all of the control group which had been infected with a higher level of the bacterium without receiving pretreatment with drugs were killed, whereas the control group inoculated with a lower level of the bacterium was killed within 7 days although 5 to 20% of the group could survive. The assay of the inhibitory effects was made using the survival rate of the mice seven days after the infection.

The results shown in Table 1 indicate that Control Compounds 1 to 3 almost failed to show effects at the higher levels of inoculation, although they gave somewhat effects at the lower levels of inoculation, whereas Compounds 1 to 5 according to the present invention exhibited excellent preventive effects even at the higher levels of inoculation.

TABLE 1

Inhibitory Effects of Synthetic Glycopeptides Intraperitoneally Administered 24 Hours prior to Subcutaneous Inoculations of E. coli, Ps. aeruginosa and K. pneumoniae SK

| | | Percent Survival* 7 Days after Inoculation (%) | | | | | |
|---|---|---|---|---|---|---|---|
| | | E. coli E77156 | | Ps. aer. No. 15 | | K. pneumo. SK | |
| Test Compound** | No. of Mice Tested | $6 \times 10^6$ (%) | $12 \times 10^6$ (%) | $3 \times 10^7$ (%) | $6 \times 10^7$ (%) | $1 \times 10^3$ (%) | $5 \times 10^3$ (%) |
| Control Compound | | | | | | | |
| 1 | 20 | 50 | 20 | 30 | 0 | 25 | 0 |
| 2 | 20 | 40 | 10 | 20 | 0 | 10 | 0 |
| 3 | 20 | 45 | 15 | 25 | 0 | 25 | 0 |
| Compound of the Invention | | | | | | | |
| 1 | 20 | 90 | 70 | 70 | 60 | 60 | 45 |
| 2 | 20 | 80 | 40 | 40 | 20 | 40 | 20 |
| 3 | 20 | 85 | 70 | 60 | 40 | 60 | 50 |
| 4 | 20 | 60 | 40 | 45 | 20 | 30 | 0 |
| 5 | 20 | 100 | 55 | 60 | 45 | 40 | 20 |

*The survival rate (percent survival) indicates the difference between the treated group and the non-treated group.
**Dosage: The dosage of each test material is 100 μg per mouse calculated as the corresponding control compound.

Control Compound 1: N-acetylmuramyl-L-alanyl-D-isoglutamine
Control Compound 2: N-acetylmuramyl-L-seryl-D-isoglutamine
Control Compound 3: N-acetylmuramyl-L-valyl-D-isoglutamine
Compound of the Invention 1: 6-O-stearoyl-N-acetyl-muramyl-L-alanyl-D-isoglutamine
Compound of the Invention 2: 6-O-stearoyl-N-acetyl-muramyl-L-seryl-D-isoglutamine
Compound of the Invention 3: 6-O-stearoyl-N-acetyl-muramyl-L-valyl-D-isoglutamine
Compound of the Invention 4: 6-O-docosanoyl-N-acetylmuramyl-L-alanyl-D-isoglutamine
Compound of the Invention 5: 6-O-triacontanoyl-N-acetyl-muramyl-L-alanyl-D-isoglutamine

EXAMPLE 2

Influence of Administration Routes on Preventive Effect

The test was conducted in the same procedures as in the test for Table 1 using different administration routes. For oral administration, the compounds of the present invention and the control compounds were suspended in 0.1% CMC aqueous solutions to give 5,000 μg/ml suspensions respectively, thereafter 0.2 ml of each suspension was orally administered (1,000 μg per mouse).

The results shown in Table 2 indicate that all of the intraperitoneal (IP), subcutaneous (SC), intravenous (IV) and oral (PO) administrations were effective and the compound of the present invention was superior over the control compound, especially remarkably superior in the case of the oral administration.

TABLE 2

Influence of Synthetic Muramyl Dipeptide Administered through Various Routes on Preventive Effect of Infection in Mice Subcutaneously Inoculated with E. coli

| Inoculation | No. of | IP | | SC | | IV | | PO | |
|---|---|---|---|---|---|---|---|---|---|
| Level (cells/mouse) | Mice Tested | A (%) | B (%) | A (%) | B (%) | A (%) | B (%) | A (%) | B (%) |
| E. coli $6 \times 10^6$ | 20 | 90 | 50 | 80 | 60 | 70 | 40 | 80 | 40 |
| E77156 $1.2 \times 10^7$ | 20 | 70 | 20 | 45 | 15 | 40 | 10 | not done | not done |

Dosage: 100 μg/mouse for IP, SC and IV administrations and 1,000 μg/mouse for PO administration.
A: Compound of the Invention 1
B: Control Compound 1

EXAMPLE 3

Influence of Dosage on Preventive Effect

The procedures of the test for Table 1 were followed except that various administration routes and dosages were employed. As shown in Table 3, in IP, SC and IV administrations, the dosages of 100 μg/mouse and 500 μg/mouse showed comparable results, with poorer results with 20 μg/mouse. In oral administration, the dosage of 200 μg/mouse showed no effect, while the dosage of 1,000 μg/mouse was effective.

TABLE 3

Influence of Dosage on Preventive Effect of Infection in Mice Subcutaneously Inoculated with *E. coli*

| | Inoculation Level (cells/mouse) | Route | No. of Mice Tested | Dosage of Compound of the Invention (μg/mouse) and Effect | | | | |
|---|---|---|---|---|---|---|---|---|
| | | | | 20 (%) | 100 (%) | 200 (%) | 500 (%) | 1,000 (%) |
| *E. coli* E77156 | $6 \times 10^6$ | ip | 10 | 40 | 90 | not done | 100 | not done |
| | | sc | 10 | 30 | 80 | not done | 90 | not done |
| | | iv | 10 | 20 | 60 | not done | 80 | not done |
| | | po | 10 | not done | not done | 0 | not done | 80 |

EXAMPLE 4

Therapeutic Effect against Candida Infection

The drug solution prepared as in the test for Table 1 was intraperitoneally or subcutaneously administered to mice at 100 or 200 μg/mouse once on the previous day of the infection in the case of one administration and each on the previous day, the day and the following day of the infection in the case of three administrations. The results, as shown in Table 4, reveal that one administration was not so effective but that three administrations gave excellent therapeutic effect. This indicates that the test compound is effective also by the post-infection administration, and therefore can be used effectively in therapy as well as prophylaxis.

TABLE 4

Therapeutic Effect against Candida IV Infection in Mice

| | Inoculation Level (cells/mouse) | No. of Mice Tested | Dosage of Compound of the Invention (μg/mouse) and Effect | |
|---|---|---|---|---|
| | | | IP (%) | SC (%) |
| *Candida albicans* DI | $2 \times 10^7$ | 10 | $100 \times 1$ | 30 | not done |
| | | 10 | $100 \times 3$ | 70 | not done |
| | | 10 | $200 \times 1$ | not done | 0 |
| | | 10 | $200 \times 3$ | not done | 80 |

EXAMPLE 5

In vitro Antibacterial Effect

In accordance with the method for measuring susceptibility by Japanese Academy of Chemotherapy, the minimum growth inhibition concentrations (MIC) of Compound of the Invention 1 and Control Compound 1 against 5 gram positive bacteria including Staphylococcus and Streptococcus, 21 gram negative bacteria including *E. coli*, Shigella and Pseudomonas and 1 Candida bacterium were determined by the agar dilution method using heat infusion agar. The results showed that the MIC's of both compounds were more than 100 μg/ml against all the bacteria, thus indicating no *in vitro* antibacterial activity.

EXAMPLE 6

Acute Toxicity Test

Compound of the Invention 1 and Control Compound were administered intraperitoneally and intravenously to STD-ddY mice, five in a group, at a dosage of 100 mg/kg. All the mice of each group survived. Therefore, the $LD_{50}$'s for both compounds in the cases of both intraperitoneally and intravenous administrations were more than 100 mg/kg.

PREPARATION 1

The following are representative examples of the synthetized higher fatty acids used as the components in the compounds according to the present invention.

Triacontanoic acid
  Melting Point: 97°–99° C.
  Elemental Analysis for $C_{30}H_{60}O_2$: Calc'd(%): C, 79.58; H, 13.36, Found (%): C, 79.35; H, 13.23.

2-Docosyltetracosanoic acid
  Melting Point: 87°–89° C.

2-Tetradecylhexadecanoic acid
  Melting Point: 73.5°–75° C.
  Elemental Analysis for $C_{30}H_{60}O_2$: Calc'd(%): C, 79.57; H, 13.36, Found (%): C, 79.57; H, 13.35.

2-Docosyl-3-hydroxyhexacosanoic acid:
  Melting Point: 89°–90° C.
  Elemental Analysis for $C_{48}H_{96}O_3$: Calc'd(%): C, 79.93; H, 13.42, Found (%): C, 79.79; H, 13.48.

3-hydroxy-2-tetradecyloctadecanoic acid:
  Melting Point: 72°–75° C.
  Elemental Analysis for $C_{32}H_{64}O_3$: Calc'd(%): C, 77.36; H, 12.98, Found (%): C, 77.46; H, 13.15.

PREPARATION 2

The physical properties of the representative compounds according to the present invention are as follows.

Compound of the Invention 1:
  Melting Point: 133°–136° C. (decomp.)
  Elemental Analysis for $C_{37}H_{66}O_{12}N_4.2H_2O$: Calc'd(%): C, 55.90; H, 8.88; N, 7.05, Found (%): C, 55.99; H, 8.57; N, 7.09.

Compound of the Invention 2:
  Melting Point: 132°–134° C. (decomp.)
  Elemental Analysis for $C_{37}H_{66}O_{13}N_4.\frac{1}{2}H_2O$ Calc'd(%): C, 57.00; H, 8.62; N, 7.19, Found (%): C, 57.00; H, 8.25; N, 6.80.

Compound of the Invention 3:
  Melting Point: 162°–165° C. (decomp.)
  Elemental Analysis for $C_{39}H_{70}O_{12}N_4.2H_2O$, Calc'd(%): C, 56.90; H, 9.08; N, 6.81, Found (%): C, 57.15; H, 8.98; N, 6.79.

Compound of the Invention 4:
  Melting Point: 153°–155° C. (decomp.)
  $[\alpha]_D^{16} + 37.0$ (THF:$H_2O$ = 10:1, C=0.5)
  Elemental Analysis for $C_{41}H_{74}O_{12}N_4.\frac{1}{2}H_2O$, Calc'd(%): C, 59.75; H, 9.18; N, 6.80, Found (%): C, 59.52; H, 9.28; N, 6.54.

Compound of the Invention 5:
  Melting Point: 182° C. (decomp.)
  Elemental Analysis for $C_{49}H_{90}O_{12}N_4$: Calc'd(%): C, 63.47; H, 9.78; N, 6.04, Found (%): C, 63.26; H, 9.81; N, 5.91.

While the invention has been described in detail and with reference to specific embodiments thereof, it will be apparent to one skilled in the art that various changes and modifications can be made therein without departing from the spirit and scope thereof.

What is claimed is:

1. A method for therapeutic treatment and/or prophylaxis of bacterial infections which comprises administering an anti-bacterial infection therapeutically effective amount or an anti-bacterial infection prophylactic effective amount of a compound selected from the group consisting of 6-O-stearoyl-N-acetylmuramyl-L-alanyl-D-isoglutamine, 6-O-stearoyl-N-acetylmuramyl-L-seryl-D-isoglutamine, 6-O-stearoyl-N-acetylmuramyl-L-valyl-D-isoglutamine, and 6-O-docosanoyl-N-acetylmuramyl-L-alanyl-D-isoglutamine to a patient who does or does not have a bacterial infection.

2. The method of claim 1 wherein said compound administered is administered in an effective dose which is effective to control *E. coli*, *P. aeruginosa* or *K. pneumoniae*.

3. The method of claim 2 wherein said compound is administered in an effective dose effective to control *C. albicans*.

4. The method of claim 1 wherein said compound is administered to said patient prior to the time when said patient exhibits a bacterial infection.

5. The method of claim 1 wherein said compound is administered to said patient prior to and after said patient exhibits a bacterial infection.

* * * * *